(12) United States Patent
Hattori et al.

(10) Patent No.: US 6,660,759 B1
(45) Date of Patent: Dec. 9, 2003

(54) 4,5-DIARYLOXAZOLE COMPOUNDS WITH PROSTAGLANDIN I$_2$ (PGI$_2$) AGONISTIC ACTIVITY

(75) Inventors: Kouji Hattori, Osaka (JP); Akira Tanaka, Osaka (JP)

(73) Assignee: Fujisawa Pharmaceutical Co. Ltd., Osaka (JP)

( * ) Notice: Subject to any disclaimer, the term of this patent is extended or adjusted under 35 U.S.C. 154(b) by 0 days.

(21) Appl. No.: 10/049,654

(22) PCT Filed: Aug. 14, 2000

(86) PCT No.: PCT/JP00/05453

§ 371 (c)(1), (2), (4) Date: Feb. 26, 2002

(87) PCT Pub. No.: WO01/16132

PCT Pub. Date: Mar. 8, 2001

(30) Foreign Application Priority Data

Aug. 30, 1999 (AU) ................................. PQ2531

(51) Int. Cl.$^7$ ..................... A61K 31/42; C07D 263/30; A61P 43/00
(52) U.S. Cl. ....................................... 514/374; 548/235
(58) Field of Search ........................... 548/235; 514/374

(56) References Cited

U.S. PATENT DOCUMENTS 5,972,965 A * 10/1999 Taniguchi et al. .......... 514/326

FOREIGN PATENT DOCUMENTS

| EP | 1 213 285 | 6/2002 |
| WO | 95 17393 | 6/1995 |
| WO | 97 03973 | 2/1997 |
| WO | 97/03973 | * 2/1997 |
| WO | 99 21843 | 5/1999 |

OTHER PUBLICATIONS

Silverman, et al, The organic Chemistry of Drug Design and Drug Action, 1986, 352–358.*

* cited by examiner

Primary Examiner—Joseph K. McKane
Assistant Examiner—Andrea D Small
(74) Attorney, Agent, or Firm—Oblon, Spivak, McClelland, Maier & Neustadt, P.C.

(57) ABSTRACT

Heterocyclic compounds of formula (I), wherein $R^1$ is carboxy or protected carboxy, $R^2$ is aryl which may have suitable sustituent(s), $R^3$ is aryl which may have suitable substituent(s), $R^4$ is hydrogen, lower alkyl, hydroxy or aryl, $A^1$ is lower alkylene, (a) is (b), etc., —$A^3$— is (c), etc. and n is 0 or 1, and pharmaceutically acceptable salts thereof which are useful as a medicament.

6 Claims, No Drawings

4.5-DIARYLOXAZOLE COMPOUNDS WITH PROSTAGLANDIN I₂ (PGI₂) AGONISTIC ACTIVITY

This application is 371 of PCT/JP00/05453 Aug. 14, 2000.

TECHNICAL FIELD

This invention relates to new heterocyclic compounds and pharmaceutically acceptable salts thereof which are useful as a medicament.

BACKGROUND ART

Some heterocyclic compounds have been known as described, for example, in WO95117393, WO95124393, WO97/03973, U.S. Pat. No. 5,362,879 and EP-A-434034.

DISCLOSURE OF INVENTION

This invention relates to new heterocyclic compounds. More particularly, this invention relates to new heterocyclic compounds and pharmaceutically acceptable salts thereof which have prostaglandin I₂ (hereinafter referred as PGI₂) agonistic activity and pharmacological activities such as an inhibitory activity on platelet aggregation, vasodilating activity, antihypertensive activity or the like, to processes for their production, to a pharmaceutical composition containing the same and to a use thereof for manufacture of medicaments.

Accordingly, one object of this invention is to provide new and useful heterocyclic compounds and pharmaceutically acceptable salts thereof.

Another object of this invention is to provide processes for production of the heterocyclic compounds and salts thereof.

A further object of this invention is to provide a pharmaceutical composition containing, as an active ingredient, said heterocyclic compounds or pharmaceutically acceptable salts thereof.

Still further object of this invention is to provide use of the heterocyclic compounds and pharmaceutically acceptable salts thereof for manufacture of medicaments for the therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension, dermatitis or the like.

The heterocyclic compounds of this invention can be represented by the following formula (I):

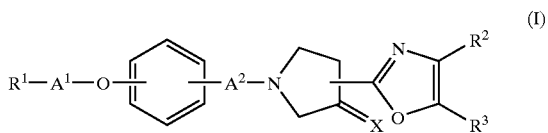

wherein $R^1$ is carboxy or protected carboxy, $R^2$ is aryl which may have substituent(s), $R^3$ is aryl which may have substituent(s), X is oxygen or a pair of hydrogen and $R^5$ (wherein $R^5$ is hydroxy or protected hydroxy), and $A^1$ and $A^2$ are each independently lower alkylene and prodrug thereof, and its salt.

According to the present invention, the new heterocyclic compounds (I) can be prepared by the processes which are illustrated in the following scheme.

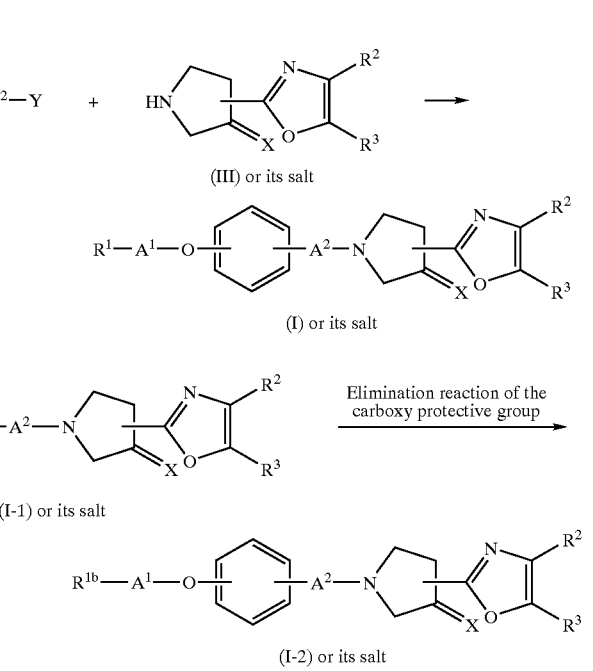

wherein $R^1$, $R^2$, $R^3$, X, $A^1$ and $A^2$ are each as defined above,

Y is leaving group, $R^{1a}$ is protected carboxy, and $R^{1b}$ is carboxy.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g.

calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

The "prodrug" means the derivatives of compounds of the present invention having a chemically or metabolically degradable group, which becomes pharmaceutically active after biotransformation.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" may include phenyl, naphthyl and the like.

Suitable "lower alkylene" may include straight one having 1 to 6 carbon atom(s), such as methylene, ethylene, trimethylene, tetramethylene, pentamethylene and hexamethylene, preferably one having 1 to 3 carbon atom(s).

Suitable "protected carboxy" may include esterified carboxy and the like. Suitable example of the ester moiety of an esterified carboxy may be the ones such as lower alkyl (e.g. methyl, ethyl, propyl, isopropyl, butyl, isobutyl, tert-butyl, pentyl, hexyl, etc.) which may have at least one substituent (s), for example, lower alkanoyloxy(lower)alkyl [e.g. acetoxymethyl, propionyloxymethyl, butyryloxymethyl, valeryloxymethyl, pivaloyloxymethyl, hexanoyloxymethyl, 1(or 2)-acetoxyethyl, 1(or 2 or 3)-acetoxypropyl, 1(or 2 or 3 or 4)-acetoxybutyl, 1(or 2)-propionyloxyethyl, 1(or 2 or 3)-propionyloxypropyl, 1(or 2)-butyryloxyethyl, 1(or 2)-isobutyryloxyethyl, (1 or 2)-pivaloyloxyethyl, 1(or 2)-hexanoyloxyethyl, isobutyryloxymethyl, 2-ethylbutyryloxymethyl, 3,3-dimethylbutyryloxymethyl, 1(or 2)-pentanoyloxyetbyl, etc.], lower alkylsulfonyl(lower) alkyl (e.g. 2-mesylethyl, etc.), mono(or di or tri)-halo(lower) alkyl (e.g. 2-iodoethyl, 2,2,2-trichloroethyl, etc.), lower alkoxycarbonyloxy(lower)alkyl (e.g. methoxycarbonyloxymethyl, ethoxycarbonyloxymethyl, 2-methoxycarbonyloxyethyl, 1-ethoxycarbonyloxyethyl, 1-isopropoxycarbonyloxyethyl, etc.), phthalidylidene (lower)alkyl or (5-lower alkyl-2-oxo-1,3-dioxol-4-yl) (lower)alkyl [e.g. (5-methyl-2-oxo-1,3-dioxol-4-yl)methyl, (5-ethyl-2-oxo-1,3-dioxol-4-yl)methyl, (5-propyl-2-oxo-1, 3-dioxol-4-yl)ethyl, etc.]; lower alkenyl (e.g. vinyl, allyl, etc.); lower alkynyl (e.g. ethynyl, propynyl, etc.); ar(lower) alkyl which may have at least one substituent(s) such as mono(or di or tri)phenyl(lower)alkyl which may have at least one substituent(s) (e.g. benzyl, 4-methoxybenzyl, 4-nitrobenzyl, phenethyl, trityl, benzhydryl, bis (methoxyphenyl)methyl, 3,4-dimethoxybenzyl, 4-hydroxy-3,5-di-tert-butylbenzyl, etc.); aryl which may have at least one substituent(s) (e.g. phenyl 4-chlorophenyl, tolyl, tert-butylphenyl, xylyl, mesityl , cumenyl, etc.); phthalidyl; and the like.

Suitable "substituent" in the term "aryl which may have substituent(s)" may include halogen, amino, hydroxy, lower alkoxy, lower alkyl as exemplified above, and the like.

Suitable "halogen" may include fluoro, chloro, bromo and iodo.

Suitable "lower alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "acyl" may include (1) lower alkanoyl (e.g. formyl, acetyl, propionyl, butyryl, isobutyryl, valeryl, isovaleryl, oxalyl, succinyl, pivaloyl, etc.); (2) lower alkane-sulfonyl (e.g. mesyl, ethanesulfonyl, propanesulfonyl, isopropanesulfonyl, butanesulfonyl, etc.); (3) arenesulfonyl (e.g. benzenesulfonyl, tosyl, etc.); (4) aroyl (e.g. benzoyl, toluoyl, xyloyl, naphthoyl, phthaloyl, indancarbonyl, etc.); (5) ar(lower)alkanoyl (e.g. phenylacetyl, phenylpropionyl, etc.); and the like.

Suitable "protected hydroxy" may include lower alkoxy as exemplified above, acyloxy, siloxy which may have one to three substituent(s), and the like.

Suitable "substituent" in the term "siloxy which may have one to three substituent(s)" may include lower alkyl as exemplified above, aryl as exemplified above, and the like.

Suitable "substituent" in the term "lower alkylene which may have substituent(s)" may include lower alkyl as exemplified above, hydroxy(lower)alkyl (e.g. hydroxymethyl, hydroxyethyl, hydroxypropyl, hydroxybutyl, hydroxypentyl, hydroxyhexyl, etc.) and the like.

Suitable "leaving group" may include halogen as exemplified above, acyloxy (e.g. acetyloxy, methanesulfonyloxy), and the like.

Preferred embodiments of the object compound (I) are as follows:

$R^1$ is carboxy or protected carboxy (more preferably esterified carboxy, most preferably lower alkoxycarbonyl), $R^2$ is aryl which may have lower alkyl (more preferably phenyl or lower alkylphenyl, most preferably phenyl), $R^3$ is aryl which may have lower alkyl (more preferably phenyl or lower alkylphenyl, most preferably phenyl), X is oxygen or a pair of hydrogen and $R^5$ (wherein $R^5$ is hydroxy or protected hydroxy, more preferably $R^5$ is lower alkoxy, most preferable $R^5$ is methoxy), and $A^1$ and $A^2$ are each independently lower alkylene (more preferably $C_1$–$C_4$ alkylene, most preferably methylene), Another preferred embodiments of the object compound (I) are as follows:

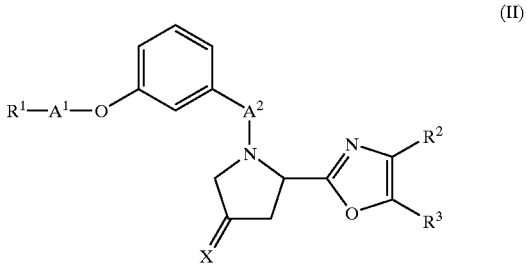

(II)

wherein $R^1$ is carboxy or lower alkoxycarbonyl (more preferably ethoxycarbonyl), $R^2$ is phenyl or lower alkylphenyl, more preferably phenyl, $R^3$ is phenyl or lower alkylphenyl, more preferably phenyl, X is oxygen or a pair of hydrogen and $R^5$ (wherein $R^5$ is hydroxy or lower alkoxy), more preferably a pair of hydrogen and lower alkoxy, most preferably a pair of hydrogen and methoxy, and $A^1$ and $A^2$ are each independently lower alkylene (more preferably methylene).

It is to be noted the object compound (I) may include one or more stereoisomers due to asymmetric carbon atom(s) and double bond, and all of such isomers and a mixture thereof are included within the scope of the present invention.

It is further to be noted isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

Also included in the scope of invention are radiorabelled derivatives of the compound of the formula (I) which are suitable for biological studies.

The processes for preparing the object and starting compounds of the present invention are explained in detail in the following.

Process 1

The compound (I) or its salt can be prepared by reacting the compound (II) or its salt with the compound (III) or its salt.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

The reaction is usually carried out in the presence of a base. Suitable base may include the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.) or the like, and the organic base such as tri(lower)alkylamino (e.g., trimethylamine, triethylamine, diisopropylethylamine, etc.), di(lower)alkylaniline (e.g. dimethylaniline, etc.), pyridine or the like.

Process 2

The compound (I-2) or its salt can be prepared by subjecting the compound (I-1) or its salt to elimination reaction of the carboxy protective group. Suitable method of this reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, 1,2-dimethoxyethane, a mixture thereof or any other solvent which does not adversely influence the reaction. A liquid base or acid can be also used as the solvent. The reaction temperature is not critical and the reaction is usually carried out under cooling to warming.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, ethyl acetate, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

The object compound (I) of this invention and pharmaceutically acceptable salt thereof have pharmacological activities such as an inhibitory activity on platelet aggregation, vasodilating activity, antihypertensive activity or the like and are prostaglandin $I_2$ agonists, and therefore can be used for treating and/or preventing thrombosis, arterial obstruction (e.g., chronic arterial obstruction, etc.), cerebrovascular disease, gastric ulcer, hepatitis, hepatic insufficiency, hepatic cirrhosis, arteriosclerosis, ischemic heart disease, restenosis or ischemic complications after coronary angioplasty (e.g., PTCA, coronary stenting, etc.), hypertension, inflammation, autoimmune disease, heart failure, renal disease (e.g., renal failure, nephritis, etc.), diabetic complication (e.g., diabetic neuropathy, diabetic nephropathy, diabetic retinopathy, etc.), peripheral circulatory disturbance, dermatitis, chilblain, baldness, bedsore, and the like, inflammatory bowel disease {such as specific inflammatory bowel disease [e.g., infectious enteritis, drug induced colitis (e.g., antibiotics associated colitis, etc), ischemic colitis, etc.], idiopathic inflammatory bowel disease (e.g., ulcerative colitis, Crohn's disease, etc) and the like }, and the like, and can be also used for protecting organs after transplantation or surgery.

Further, the object compound (I) and pharmaceutically acceptable salt thereof can be also used as a component for organ preserving fluids and as an agent for inhibiting metastasis of cancer.

The object compound (I) was confirmed to have a potent $PGI_2$ agonistic activity. Further in order to show the inhibitory activity on platelet aggregation, pharmacological data of the representative compounds thereof are shown in the following.

Inhibition of Human Platelet Aggregation Induced by ADP

[I] Test Compound:
(1) Sodium 3-{[(2R, 4R)-2-(4,5-dipbenyloxazol-2-yl)-4-methoxypyrrolidin-1-yl]methyl}phenoxyacetate
(2) Sodium 3-{[(2R, 4S)-2-(4,5-diphenyloxazol-2-yl)-4-methoxypyrrolidin-1-yl]methyl}phenoxyacetate

[II] Test Method:

Human blood was obtained from healthy volunteers and mixed with 1/10 volume of 3.8% sodium citrate, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATRACER 801 (NBS, Japan), a 8 channel aggregometer. The test compound solution (25 μl) and the PRP (225 μl) were mixed and stirred at 1000 rpm at 37° C. for 2 minutes. Aggregation was induced by ADP solution at the final concentration of 2.5 μM.

[III] Test Result:

| Test Compound | $IC_{50}$ |
|---|---|
| (1) | $<1 \times 10^{-7}$ M |
| (2) | $<1 \times 10^{-7}$ M |

The active ingredient of this invention can be used in a form of a pharmaceutical preparation, for example, in solid, semisolid or liquid form, which contains a compound (I), as an active ingredient, in admixture with an organic or inorganic carrier or excipient suitable for external, enteral, intravenous, intramuscular, parenteral or intramucous applications. The active ingredient may be compounded, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient may be compounded into, for example, preparations for oral application, preparations for injection, preparations for external application, preparations for inhalation, preparations for application to mucous membranes.

The effective ingredient may usually be administered with a unit dose of 0.01 mg/kg to 50 mg/kg, 1 to 4 times a day. However, the above dosage may be increased or decreased according to age, weight, and conditions of the patient or the administering method.

The compound (I) of the present invention has much advantage, such as more selective $PGI_2$ antagonitic activity, stronger activity, more suitable half-life, decreased adverse effect, or the like, compared to the known heterocyclic compounds having the $PGI_2$ antagonitic activity.

The patents, patent applications and publications cited herein above are incorporated by reference.

Abbreviations used in this application are as follows:

| | |
|---|---|
| THF | Tetrahydrofuran |
| EtOAc | Ethyl acetate |
| DMSO | Dimethyl sulfoxide |
| DMF | N,N-Dimethylformamide |
| TBDMSCl | tert-Butyldimethylsilyl chloride |
| EtOH | Ethyl alcohol |
| MeOH | Methyl alcohol |
| $Et_2O$ | Diethyl ether |
| $AcONH_4$ | Ammonium acetate |
| AcOH | Acetic acid |
| MeCN | Actonitrile |

The following Preparations and Examples are given only for the purpose of illustrating the present invention in more detail.

PREPARATION 1

A suspension of cis4-hydroxy-D-proline (10.0 g) in THF-water (1:1, 100 mL) was added 1N NaOH solution (50 mL) at 5° C. To the mixture was added a solution of benzyloxycarbonyl chloride (12.5 mL) in THF (10 mL) keeping pH to 8.5–10 by the addition of 2N NaOH solution at 5–10° C. After stirring at the same temperature for 1 h, the reaction mixture was washed with EtOAc (50 mL), adjusted to pH 2 by the addition of 4N HCl, and extracted with EtOAc. The organic layer was washed with water and brine, dried ($MgSO_4$), and evaporated in vacuo to give cis4-hydroxy-N-benzyloxycarbonyl-D-proline (18.74 g).

IR (neat): 3433, 2952, 1680, 1427, 1358, 1209 $cm^{-1}$; NMR (DMSO-$d_6$, δ): 1.80–2.03 (1H, m), 2.21–2.45 (1H, m), 3.14–3.30 (1H, m), 3.50–3.66 (1H, m), 4.13–4.35 (2H, m), 4.96–5.15 (2H, m), 7.20–7.45 (5H, m); ESI-MS m/z: 288 (M+$Na^+$).

PREPARATION 2

To a mixture of cis4-hydroxy-N-benzyloxycarbonyl-D-proline (18.74 g) and imidazole (11.56 g) in DMF (100 mL) was added TBDMSCl (23.36 g) at 5° C. After stirring at room temperature for 16 hours, the reaction mixture was diluted with EtOAc-hexane (1:1, 600 mL), washed with 1N HCl, water and brine, dried ($MgSO_4$), and evaporated in vacuo. The residue was dissolved in MeOH-THF (3:1, 400 mL). To the solution was added an aqueous solution (100 mL) of $K_2CO_3$ (9.77 g) at 5° C., and the mixture was stirred at the same temperature for 1 hour. The organic solvent was evaporated, and the residue was adjusted to pH 2 by the addition of 3N HCl, and extracted with EtOAc. The organic layer was washed with water and brine, dried ($MgSO_4$), and evaporated in vacuo. The residue was purified by silica gal column chromatography to give cis-4-(tert-butyldimethylsilyloxy)-N-benzyloxycarbonyl-D-proline (23.99 g).

IR (neat): 3433, 2952, 1680, 1427, 1358, 1209 cm$^{-1}$; NMR (DMSO-d$_6$, δ): 0.03 and 0.04 (total 6H, each s), 0.80 and 0.81 (total 9H, each s), 1.80–2.00 (1H, m), 2.22–2.45 (1H, m), 3.10–3.22 (1H, m), 3.50–3.68 (1H, m), 4.17–4.45 (2H, m), 4.94–5.13 (2H, m), 7.21–7.40 (5H, m); Negative ESI-MS m/z: 378 (M–H)$^-$.

PREPARATION 3

To a mixture of cis4-(tert-butyldimethylsilyloxy)-N-benzyloxycarbonyl-D-proline (21.87 g), benzoin (12.25 g), and 4-dimethylaminopyridine (7.04 g) in CH$_2$Cl$_2$ (200 mL) was added 1-ethyl-3-(3'-dimethylaminopropyl)carbodiimide (10.52 mL) at 5° C., and the mixture was stirred at room temperature for 20 hours. The reaction mixture was evaporated, and the residue was dissolved in EtOAc (250 mL), washed with 1N HCl (150 mL), water, saturated sodium hydrogen carbonate solution, water and brine, dried (MgSO$_4$), and evaporated in vacuo. The residue was purified by silica gal column chromatography (hexane-EtOAc, 5:2 elution) to give cis4-(tert-butyldimethylsilyloxy)-N-benzyloxycarbonyl-D-proline 2-oxo-1,2-diphenylethyl ester (21.62 g).

IR (neat): 3469, 3064, 2952, 2856, 1757, 1707, 1597, 1496, 1450, 1417, 1356 cm$^{-1}$; NMR (DMSO-d$_6$, δ): 0.00–0.15 (6H, m), 0.80–0.93 (9H, m), 1.98–2.27 (1H, m), 2.40–2.73 (1H, m), 3.15–3.30 (1H, m), 3.60–3.83 (1H, m), 4.42–4.75 (2H, m), 5.05–5.19 (2H, m), 6.05–6.17 (1H, m), 6.98–8.15 (15H, m); ESI-MS m/z: 596 (M+Na$^+$).

PREPARATION 4

To a solution of cis-4-(tert-butyldimethylsilyloxy)-N-benzyloxycarbonyl-D-proline 2-oxo-1,2-diphenylethyl ester (21.62 g) in MeOH-THF (2:1, 380 mL) was added 1N HCl (76 mL) at 5° C., and the mixture was stirred at room temperature for 24 hours. To the reaction mixture was added NaHCO$_3$ (6.7 g) at 5° C. The organic solvent was evaporated, and the residue was extracted with EtOAc. The organic layer was washed with water and brine, dried (MgSO$_4$), and evaporated in vacuo. The residue was purified by silica gal column chromatography (hexane-EtOAc, 2:1~1:3 elution) to give cis4-hydroxy-N-benzyloxycarbonyl-D-proline 2-oxo-1,2-diphenylethyl ester (13.90 g).

IR (KBr): 3465, 3062, 2951, 1755, 1695, 1597, 1417, 1354 cm$^{-1}$; NMR (DMSO-d$_6$, δ): 1.94–2.19 (1H, m), 2.30–2.65 (1H, m), 3.08–3.27 (1H, m), 3.50–3.74 (1H, m), 4.17–4.65 (2H, m), 4.94–5.16 (3H, m), 7.05–7.70 (13H, m), 7.99–8.13 (2H, m); ESI-MS m/z: 482 (M+Na$^+$).

PREPARATION 5

A mixture of cis-4-hydroxy-N-benzyloxycarbonyl-D-proline 2-oxo-1,2-diphenylethyl ester (7.0 g) and AcONH$_4$ (11.8 g) in AcOH was stirred at 120° C. for 1 hour. The reaction mixture was evaporated, and the residue was dissolved in EtOAc, washed with water, 3N NaOH solution, water and brine, dried (MgSO$_4$), and evaporated in vacuo. The residue was purified by silica gal column chromatography (hexane-EtOAc, 1:1~2:3 elution) to give first benzyl (2R, 4R)-4-acetoxy-2-(4,5-diphenyloxazol-2-yl) pyrrolidine-1-carboxylate (972.6 mg), then benzyl (2R, 4R)-2-(4,5-diphenyloxazol-2-yl)-4-hydroxypyrrolidine-1-carboxylate (5.12 g).

Benzyl (2R, 4R)-2-(4,5-Diphenyloxazol-2-yl)-4-hydroxypyrrolidine-1-carboxylate

IR (neat): 3367, 3060, 2951, 1707, 1446, 1414, 1356, 1209 cm$^{-1}$; NMR (CDCl$_3$δ): 2.33–2.63 (2H, m), 3.68–3.93 (2H, m), 4.45–4.61 (1H, m), 4.98–5.28 (3H, m), 5.90–6.10 (1H, m), 7.08–7.70 (15H, m); APCI-MS m/z: 441 (M+H$^+$).

Benzyl (2R, 4R)-4-Acetoxy-2-(4,5-diphenyloxazol-2-yl) pyrrolidine-1-carboxylate

IR (neat): 3060, 3033, 2951, 1739, 1711, 1500, 1446, 1414, 1354 cm$^{-1}$; NMR (CDCl$_3$δ): 1.85 (3H, s), 2.55–2.73 (2H, m), 3.72–4.03 (2H, m), 4.97–5.40 (4H, m), 7.05–7.70 (15H, m); APCI-MS m/z: 483 (M+H$^+$).

PREPARATION 6

To a solution of benzyl (2R, 4R)-2-(4,5-diphenyloxazol-2-yl)-4-hydroxypyrrolidine-1-carboxylate (350 mg) in MeOH (15 mL) was added 10%Pd-C (wet) (50 mg), and the mixture was stirred under hydrogen atmosphere at room temperature for 1 hour. The catalyst was removed by filtration and the filtrate was evaporated to give (2R, 4R)-2-(4, 5-diphenyloxazol-2-yl)pyrrolidin-4-ol (236.8 mg).

IR (neat): 3319, 3059, 2941, 1589, 1568, 1502, 1444, 1217, 1061 cm$^{-1}$; NMR (CDCl$_3$, δ): 2.25–2.53 (2H, m), 3.14–3.28 (1H, m), 3.27 (1H, dd, J=11.7, 4.5 Hz), 4.45–4.57 (2H, m), 7.25–7.45 (6H, m), 7.50–7.70 (4H, m); APCI-MS m/z: 307 (M+H$^+$).

PREPARATION 7

The following compounds (I) to (3) were obtained according to the similar manner to that of preparation 6.

(1) (2R, 4S)-2-(4,5-Diphenyloxazol-2-yl)pyrrolidin-4-ol

IR (KBr): 3280, 3145, 2883, 1603, 1566, 1444, 1329, 1221, 1061 cm$^{-1}$; NMR (CDCl$_3$, δ): 2.20–2.38 (1H, m), 2.38–2.55 (1H, m), 3.00–3.12 (1H, m), 3.30 (1H, dd, J=11.6, 4.2 Hz), 4.55–4.68 (1H, m), 4.69 (1H, dd, J=7.6, 7.6 Hz), 7.25–7.45 (6H, m), 7.50–7.70 (4H, m); APCI-MS m/z: 307 (M+H$^+$).

(2) 2-[(2R, 4R)-4-Methoxypyrrolidin-2-yl]-4,5-diphenyloxazole

IR (neat): 3319, 3059, 2929, 2823, 1604, 1568, 1502, 1444, 1358, 1219 cm$^{-1}$; NMR (CDCl$_3$δ): 2.18–2.34 (1H, m), 2.42–2.57 (1H, m), 3.02–3.12 (1H, dd, J=11.8, 5.0 Hz), 3.25–3.35 (1H, m), 3.32 (3H, s), 3.99–4.10 (1H, m), 4.37 (1H, dd, J=8.4, 6.8 Hz), 7.25–7.43 (6H, m), 7.51–7.70 (4H, m); APCI-MS m/z: 321 (M+H$^+$).

(3) 2-[(2R, 4S)-4-Methoxypyrrolidin-2-yl]-4,5-diphenyloxazole

IR (neat): 3330, 3057, 2929, 2823, 1604, 1568, 1502, 1444, 1356, 1219 cm$^{-1}$; NMR (CDCl$_3$, δ): 2.32–2.42 (2H, m), 3.07–3.30 (2H, m), 3.35 (3H, s), 4.04–4.15 (1H, m), 4.61 (1H, dd, J=7.6, 7.6 Hz), 7.25–7.45 (6H, m), 7.50–7.68 (4H, m); APCI-MS m/z: 321 (M+H$^+$).

PREPARATION 8

To a mixture of benzyl (2R, 4R)-2-(4,5-diphenyloxazol-2-yl)-4-hydroxypyrrolidine-1-carboxylate (1.50 g) and triphenylphosphine (1.43 g) in THF (15 mL) was added diethyl azodicarboxylate (0.86 mL) at 5° C., and the mixture was stirred at the same temperature for 30 minutes. To the mixture was added AcOH (0.29 mL) at 5° C., and the mixture was stirred at room temperature for 3 hours. The reaction mixture was evaporated, and the residue was dissolved in EtOAc, washed with saturated sodium hydrogen carbonate solution, water and brine, dried (MgSO$_4$), and evaporated in vacuo. The residue was purified by silica gal column chromatography (hexane-EtOAc, 2:1 elution) to give benzyl (2R, 4S)-4-acetoxy-2-(4,5-diphenyloxazol-2-yl)pyrrolidine-1-carboxylate (1.88 g).

IR (neat): 2983, 1743, 1712, 1500, 1446, 1415, 1358 cm$^{-1}$; NMR (CDCl$_3$, δ): 2.09 (3H, s), 2.50–2.63 (2H, m), 3.70–4.03 (2H, m), 4.90–5.35 (3H, m), 5.38–5.50 (1H, m), 7.02–7.70 (15H, m); APCI-MS m/z: 483 (M+H$^+$).

PREPARATION 9

To a solution of benzyl (2R, 4S)-4-acetoxy-2-(4,5-diphenyloxazol-2-yl)pyrrolidine-1-carboxylate (1.49 g) in MeCN (15 mL) was added 28% sodium methylate in MeOH (0.72 mL) at 5° C., and the mixture was stirred at the same temperature for 30 minutes. To the reaction mixture was added 1N HCl (3.8 mL) under ice-cooling, and extracted with EtOAc. The organic layer was washed with water, saturated sodium hydrogen carbonate solution, water and brine, dried (MgSO$_4$), and evaporated in vacuo. The residue was purified by silica gal column chromatography (hexane-EtOAc, 1:3 elution) to give benzyl (2R, 4S)-2-(4,5-diphenyloxazol-2-yl)-4-hydroxypyrrolidine-1-carboxylate (980.8 mg).

IR (neat): 3433, 3060, 2949, 1707, 1500, 1446, 1417, 1356 cm$^{-1}$; NMR (CDCl$_3$, δ): 2.37–2.53 (2H, m), 3.60–3.92 (2H, m), 4.60–4.74 (1H, m), 4.87–5.35 (3H, m), 7.00–7.70 (15H, m); APCI-MS m/z: 441 (M+H$^+$).

PREPARATION 10

To a solution of benzyl (2R, 4R)-2-(4,5-diphenyloxazol-2-yl)-4-hydroxypyrrolidine-1-carboxylate (400 mg) and CH$_3$I (0.57 mL) in DMF (5 mL) was added NaH (60% oil suspension, 48 mg) at 5° C. The mixture was stirred at the same temperature for 10 minutes, then stirred at room temperature for 30 minutes. The reaction mixture was poured into diluted HCl, and extracted with EtOAc. The organic layer was washed with water, saturated sodium hydrogen carbonate, water and brine, dried (MgSO$_4$), and evaporated in vacuo. The residue was purified by silica gal column chromatography (hexane-EtOAc, 1:1 elution) to give benzyl (2R, 4R)-2-(4,5-diphenyloxazol-2-yl)-4-methoxypyrrolidine-1-carboxylate (402.9 mg).

IR (neat): 3062, 2943, 1709, 1444, 1414, 1354, 1213, 1095 cm$^{-1}$; NMR (CDCl$_3$δ): 2.45–2.65 (2H, m), 3.30 (3H, s), 3.60–4.18 (3H, m), 4.93–5.32 (3H, m), 7.02–7.75 (15H, m); APCI-MS m/z: 455 (M+H$^+$).

PREPARATION 11

The following compound was obtained according to the similar manner to that of preparation 10.
Benzyl (2R, 4S)-2-(4,5-Diphenyloxazol-2-yl)-4-methoxypyrrolidine-1-carboxylate IR (neat): 3060, 2939, 1711, 1446, 1414, 1354, 1117, 1095 cm$^{-1}$; NMR (CDCl$_3$δ): 2.35–2.61 (2H, m), 3.37 (3H, s), 3.65–3.94 (2H, m), 4.09–4.23 (1H, m), 4.87–5.28 (3H, m), 7.00–7.68 (15H, m); APCI-MS m/z: 455 (M+H$^+$).

EXAMPLE 1

To a mixture of (2R, 4R)-2-(4,5-diphenyloxazol-2-yl)pyrrolidin-4-ol (229 mg) and potassium carbonate (155 mg) in DMF (5 mL) was added ethyl 3-(bromomethyl)phenoxyacetate (245 mg) at 5° C. and stirred at the same temperature for 30 minutes then at room temperature for 16 hours. The reaction mixture was diluted with EtOAc, washed with water and brine, dried (MgSO$_4$), and evaporated in vacuo. The residue was purified by silica gel column chromatography (hexane-EtOAc, 1:2) to give ethyl 3-{[(2R, 4R)-2-(4,5-diphenyloxazol-2-yl)-4-hydroxypyrrolidin-1-yl]methyl}phenoxyacetate (359.7 mg).

IR (neat): 3386, 3057, 2979, 2804, 1759, 1601, 1591, 1487, 1444 cm$^{-1}$; NMR (CDCl$_3$, δ): 1.27 (3H, t, J=7.1 Hz), 2.15–2.32 (1H, m), 2.45–2.68 (1H, m), 2.87–3.02 (2H, m), 3.60–3.85 (2H, m), 4.04 (1H, dd, J=8.7, 3.3 Hz), 4.23 (2H, q, J=7.1 Hz), 4.30–4.55 (1H, m), 4.50 (2H, s), 6.65–6.79 (1H, m), 6.82–7.00 (2H, m), 7.05–7.45 (7H, m), 7.45–7.68 (4H, m); APCI-MS m/z: 499 (M+H$^+$).

EXAMPLE 2

The following compounds (I) to (3) were obtained according to a similar manner to that of example 1.
(1) Ethyl 3-{[(2R, 4S)-2-(4,5-Diphenyloxazol-2-yl)-4-hydroxypyrrolidin-1-yl]methyl}phenoxyacetate IR (neat): 3384, 3057, 2979, 2925, 2814, 1759, 1601, 1591, 1487, 1444 cm$^{-1}$; NMR (CDCl$_3$δ): 1.27 (3H, t, J=7.1 Hz), 1.78 (1H, d, J 5.1 Hz), 2.15–2.30 (1H, m), 2.47–2.72 (2H, m), 3.46 (1H, dd, J=10.2, 5.7 Hz), 3.69 (1H, d, J=13.4 Hz), 3.87 (1H, d, J=13.4 Hz), 4.23 (1H, dd, J=7.7, 7.7 Hz), 4.23 (2H, q, J=7.1 Hz), 4.50 (2H, s), 4.50–4.70 (1H, m), 6.70–6.78 (1H, m), 6.85–7.00 (2H, m), 7.17 (1H, dd, J=7.7, 7.7 Hz), 7.25–7.45 (6H, m), 7.50–7.68 (4H, m); APCI-MS m/z: 499 (M+H$^+$).
(2) Ethyl 3{[(2R, 4R)-2-(4,5-Diphenyloxazol-2-yl)-4-methoxypyrrolidin-1-yl]methyl}phenoxyacetate IR (neat): 3057, 2979, 2929, 2819, 1759, 1601, 1589, 1487, 1444, 1377 cm$^{-1}$; NMR (CDCl$_3$, δ): 1.27 (3H, t, J=7.1 Hz), 2.28–2.68 (3H, m), 3.16–3.27 (1H, m), 3.33 (3H, s), 3.57 (1H, d, J=13.4 Hz), 3.79 (1H, dd, J=8.3, 8.3 Hz), 3.91 (1H, d, J=13.4 Hz), 3.90–4.05 (1H, m), 4.23 (2H, q, J=7.1 Hz), 4.49 (2H, s), 6.67–6.77 (1H, m), 6.88–7.02 (2H, m), 7.17 (1H, dd, J=7.9, 7.9 Hz), 7.22–7.41 (6H, m), 7.52–7.68 (4H, m); APCI-MS m/z: 513 (M+H$^+$).
(3) Ethyl 3-{[(2R, 4S)-2-(4,5-Diphenyloxazol-2-yl)-4-methoxypyrrolidin-1-yl]methyl}phenoxyacetate IR (neat): 3059, 2981, 2931, 2821, 1759, 1601, 1589, 1487, 1444, 1375 cm$^{-1}$; NMR (CDCl$_3$, δ): 1.27 (3H, t, J=7.1 Hz), 2.20–2.36 (1H, m), 2.40–2.58 (2H, m), 3.31 (3H, s), 3.46 (1H, dd, J=10.1, 6.1 Hz), 3.63 (1H, d, J=13.3 Hz), 3.90 (1H, d, J=13.3 Hz), 4.00–4.18 (2H, m), 4.23 (2H, q, J=7.1 Hz), 4.48 (2H, s), 6.67–6.76 (1H, m), 6.85–6.97 (2H, m), 7.17 (1H, dd, J=7.8, 7.8 Hz), 7.25–7.43 (6H, m), 7.50–7.67 (4H, m); APCI-MS m/z: 513 (M+H$^+$).

EXAMPLE 3

To a solution of ethyl 3-{[(2R, 4R)-2-(4,5-diphenyloxazol-2-yl)-4-hydroxypyrrolidin-1-yl]methyl}phenoxyacetate (353 mg) in MeOH:1,4-dioxane (1:1, 10 mL) was added 1N NaOH solution (0.744 mL) at 5° C., and the mixture was stirred at room temperature for 4 hours. The reaction mixture was evaporated and Et$_2$O was added thereto. The resulting solid was collected by filtration to give sodium 3-[(2R, 4R)-2-(4,5-diphenyloxazol-2-yl)-4-hydroxypyrrolidin-1-ylmethyl]phenoxyacetate (327.7 mg).

IR (KBr): 3381, 3057, 2947, 2802, 1608, 1487, 1423, 1338 cm$^{-1}$; NMR (DMSO-d$_6$, δ): 2.00–2.20 (1H, m), 2.47–2.67 (2H, m), 2.82–2.98 (1H, m), 3.40 (1H, d, J=14.8 Hz), 3.73–3.93 (2H, m), 4.03 (2H, s), 4.20–4.38 (1H, m), 4.98 (1H, br), 6.58–6.68 (1H, m), 6.70–6.83 (2H, m), 7.09 (1H, dd, J=7.9, 7.9 Hz), 7.30–7.63 (10H, m); ESI-MS m/z: 493 (M+H$^+$).

EXAMPLE 4

The following compounds (I) to (4) were obtained according to the similar manner to that of Example 3.

(1) Sodium 3-{[(2R)-2-(4,5-Diphenyloxazol-2-yl)-4-oxopyrrolidin-1-yl]methyl}phenoxyacetate IR (KBr): 3379, 3057, 2924, 1761, 1606, 1487, 1423, 1336, 1261 cm$^{-1}$; NMR (DMSO-d$_6$, δ): 2.72–3.00 (2H, m), 3.07 (1H, d, J=17.6 Hz), 3.29 (1H, d, J=17.6 Hz), 3.67 (1H, d, J=13.3 Hz), 3.82 (1H, d, J=13.3 Hz), 4.03 (2H, s), 4.50 (1H, dd, J=7.1, 7.1 Hz), 6.57–6.85 (3H, m), 7.02–7.17 (1H, m), 7.20–7.65 (10H, m); ESI-MS m/z: 491 (M+H$^+$).

(2) Sodium 3-{[(2R, 4S)-2-(4,5-Diphenyloxazol-2-yl)-4-hydroxypyrrolidin-1-yl]methyl}phenoxyacetate IR (KBr): 3384, 3059, 2835, 1603, 1489, 1425, 1338, 1261 cm$^{-1}$; NMR (DMSO-d$_6$, δ): 1.97–2.13 (1H, m), 2.25–2.47 (2H, m), 3.24 (1H, dd, J=9.8, 5.9 Hz), 3.55 (1H, d, J=13.3 Hz), 3.80 (1H, d, J=13.3 Hz), 4.02 (2H, s), 4.00–4.13 (1H, m), 4.30–4.43 (1H, m), 6.57–6.68 (1H, m), 6.68–6.82 (2H, m), 7.08 (1H, dd, J=7.9, 7.9 Hz), 7.30–7.62 (10H, m); ESI-MS m/z: 493 (M+H$^+$).

(3) Sodium 3-{[(2R, 4R)-2-(4,5-Diphenyloxazol-2-yl)-4-methoxypyrrolidin-1-yl]methyl}phenoxyacetate IR (KBr): 3421, 3059, 2927, 2821, 1606, 1489, 1425, 1336, 1261 cm$^{-1}$; NMR (DMSO-d$_6$, δ): 2.08–2.26 (1H, m), 2.40–2.70 (2H, m), 2.97–3.10 (1H, m), 3.19 (3H, s), 3.43 (1H, d, J=12.7 Hz), 3.70–3.90 (2H, m), 3.90–4.10 (1H, m), 4.01 (2H, s), 6.55–6.68 (1H, m), 6.68–6.83 (2H, m), 7.09 (1H, dd, J=8.1, 8.1 Hz), 7.30–7.63 (10H, m); ESI-MS m/z: 507 (M+H$^+$).

(4) Sodium 3-{[(2R, 4S)-2-(4,5-Diphenyloxazol-2-yl)-4-methoxypyrrolidin-1-yl]methyl}phenoxyacetate IR (KBr): 3384, 3057, 2925, 2821, 1606, 1489, 1425, 1338, 1261 cm$^{-1}$; NMR (DMSO-d$_6$, δ): 2.12–2.55 (3H, m), 3.22 (3H, s), 3.18–3.42 (1H, m), 3.54 (1H, d, J=13.3 Hz), 3.79 (1H, d, J=13.3 Hz), 3.95–4.17 (2H, m), 4.02 (2H, s), 6.57–6.70 (1H, m), 6.70–6.85 (2H, m), 7.09 (1H, dd, J=8.0, 8.0 Hz), 7.30–7.60 (10H, m); ESI-MS m/z: 507 (M+H$^+$).

EXAMPLE 5

To a solution of oxalyl chloride (0.050 mL) in CH$_2$Cl$_2$ (10 mL) was added a solution of DMSO (0.061 mL) in CH$_2$Cl$_2$ (0.5 mL) keeping the temperature below −55° C., and stirred for 30 minutes. To the mixture was added a solution of ethyl 3-{[(2R, 4R)-2-(4,5-diphenyloxazol-2-yl)-4-hydroxypyrrolidin-1-yl]methyl}phenoxyacetate (238 mg) in CH$_2$Cl$_2$ (3 mL) at the same temperature, then stirred for 1 hour. To the reaction mixture was added triethylamine (0.27 mL), and warmed to room temperature over 30 minutes. After stirring at the same temperature for 30 minutes, the mixture was diluted with EtOAc, washed with water, saturated sodium hydrogen carbonate, water and brine, dried (MgSO$_4$), evaporated. The residue was purified by silica gel column chromatography (hexane-EtOAc 2:1) to give ethyl 3-{[(2R)-2-(4,5-diphenyloxazol-2-yl)-4-oxopyrrolidin-1-yl]methyl}phenoxyacetate (191.8 mg).

IR (neat): 3059, 2981, 2931, 2802, 1761, 1603, 1591, 1487, 1446, 1205 cm$^{-1}$; NMR (CDCl$_3$δ): 1.27 (3H, t, J=7.1 Hz), 2.77–3.05 (2H, m), 3.03 (1H, d, J=17.2 Hz), 3.48 (1H, d, J=17.2 Hz), 3.73 (1H, d, J=13.4 Hz), 3.92 (1H, d, J=13.4 Hz), 4.24 (2H, q, J=7.1 Hz), 4.42 (1H, dd, J=7.3, 7.3 Hz), 4.53 (2H, s), 6.72–6.82 (1H, m), 6.88–6.99 (2H, m), 7.15–7.45 (7H, m), 7.50–7.70 (4H, m); APCI-MS m/z: 497 (M+H$^+$).

EXAMPLE 6

To a solution of Ethyl 3-{[(2R, 4S)-2-(4,5-diphenyloxazol-2-yl)-4-methoxypyrrolidin-1-yl]methyl}phenoxyacetate (3.00 g) in EtOH (30 mL) was added 1N NaOH solution (6.00 mL) at 5° C., and the mixture was stirred at room temperature for 1 hour. To the reaction mixture was added 1N HCl (6.00 mL) at 5° C. and evaporated. The residue was extracted with EtOAc, washed with water and brine, dried (Na$_2$SO$_4$), and evaporated in vacuo to give 3-{[(2R, 4S)-2-(4,5-diphenyloxazol-2-yl)-4-methoxypyrrolidin-1-yl]methyl}phenoxyacetic acid (2.75 g).

IR (KBr): 3433, 3057, 2931, 2823, 1736, 1591, 1487, 1444, 1225 cm$^{-1}$; NMR (DMSO-d$_6$, δ): 2.13–2.30 (1H, m), 2.30–2.55 (2H, m), 3.22 (3H, s), 3.20–3.35 (1H, m), 3.60 (1H, d, J=13.5 Hz), 3.80 (1, d, J=13.5 Hz), 3.95–4.18 (2H, m), 4.54 (2H, s), 6.68–6.78 (1H, m), 6.81–6.93 (2H, m), 7.16 (1H, dd, J=7.8, 7.8 Hz), 7.32–7.62 (10H, m); ESI-MS m/z: 485 (M+H$^+$).

EXAMPLE 7

To a solution of 3-{[(2R, 4S)-2-(4,5-diphenyloxazol-2-yl)-4-methoxypyrrolidin-1-yl]methyl}phenoxyacetic acid (100 mg) in EtOH (0.65 mL) was added a solution of L-(+)-tartaric acid (32 mg) in EtOH (1.3 mL) at room temperature. To the mixture was added n-hexane (3.9 mL), and the mixture was stirred at room temperature for 2 hours. The resulting precipitate was collected and dried under reduced pressure to give 3-{[(2R, 4S)-2-(4,5-diphenyloxazol-2-yl)-4-methoxypyrrolidin-1-yl] methyl}phenoxyacetic acid tartrate (a L-(+)-tartaric acid addition salt of 3-{[(2R, 4S)-2-(4,5-diphenyloxazol-2-yl)-4-methoxypyrrolidin 1-yl]methyl}phenoxyacetic acid) (102 mg).

IR(KBr): 3435, 3028, 2924, 2854, 1722, 1604, 1448, 1412 cm$^{-1}$; NMR (DMSO-d$_6$, δ): 2.12–2.30 (1H, m), 2.30–2.55 (2H, m), 3.22 (3H, s), 3.20–3.35 (1H, m), 3.61 (1H, d, J=13.6 Hz), 3.80 (1, d, J=13.6 Hz), 3.95–4.18 (2H, m), 4.30 (2H, s), 4.54 (2H, s), 6.68–6.78 (1H, m), 6.82–6.94 (2H, m), 7.16 (1H, dd, J=7.8, 7.8 Hz), 7.30–7.60 (10H, m).

What is claimed is:

1. A compound of the formula:

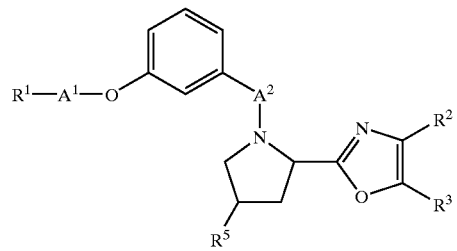

wherein $R^1$ is carboxy or lower alkoxycarbonyl, $R^2$ is phenyl or lower alkylphenyl, $R^3$ is phenyl or lower alkylphenyl, and $R^5$ is hydroxy or lower alkoxy, and $A^1$ and $A^2$ are each independently methylene.

2. The compound of claim 1, wherein $R^1$ is carboxy or ethoxycarbonyl, $R^2$ is phenyl, and $R^3$ is phenyl.

3. The compound according to claim 1, which is a compound selected from the group consisting of (1) ethyl 3-{[(2R, 4R)-2-(4,5-diphenyloxazol-2-yl)-4-hydroxypyrrolidin-1-yl]methyl}phenoxyacetate, (2) ethyl 3-{[(2R, 4S)-2-(4,5-diphenyloxazol-2-yl)-4-hydroxypyrrolidin-1-yl]methyl}phenoxyacetate, (3) ethyl 3-{[(2R, 4R)-2-(4,5-diphenyloxazol-2-yl)-4-methoxypyrrolidin-1-yl]methyl}phenoxyacetate, (4) ethyl 3-{[(2R, 4S)-2-(4,5-diphenyloxazol-2-yl)-4-methoxypyrrolidin-1-yl]methyl}phenoxyacetate, (5) sodium 3-[(2R, 4R)-2-(4,5-diphenyloxazol-2-yl)-4-hydroxypyrrolidin-1-ylmethyl]phenoxyacetate, (6) sodium 3-{[(2R, 4S)-2-(4,5-diphenyloxazol-2-yl)-4-hydroxypyrrolidin-1-yl]methyl}phenoxyacetate, (7) sodium 3-{[(2R, 4R)-2-(4,5-diphenyloxazol-2-yl)-4-methoxypyrrolidin-1-yl]methyl}phenoxyacetate, (8) sodium 3-{[(2R, 4S)-2-(4,5-diphenyloxazol-2-yl)-4-methoxypyrrolidin-1-yl]methyl}phenoxyacetate, (9) 3-{[(2R, 4S)-2-(4,5-diphenyloxazol-2-yl)-4-methoxypyrrolidin-1-yl]methyl}phenoxyacetic acid, and

(10) 3-{[(2R, 4S)-2-(4,5-diphenyloxazol-2-yl)-4-methoxypyrrolidin-1-yl]methyl}phenoxyacetic acid tartrate.

4. A process for preparing a compound of the formula:

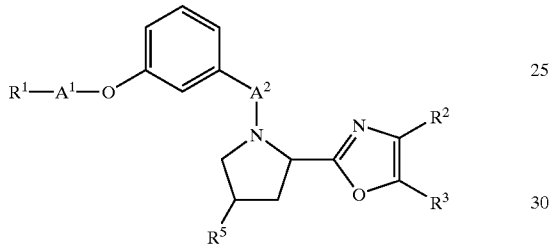

wherein $R^1$ is carboxy or protected carboxy, $R^2$ is phenyl or lower alkylphenyl, $R^3$ is phenyl or lower alkylphenyl, $R^5$ is hydroxy or lower alkoxy, and $A^1$ and $A^2$ are each independently methylene and a prodrug thereof, and its salt, which comprises (1) reacting a compound of the formula:

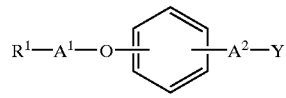

or its salt with a compound of the formula:

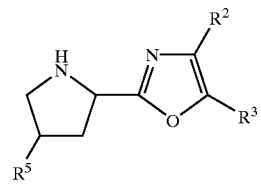

or its salt to give a compound of the formula:

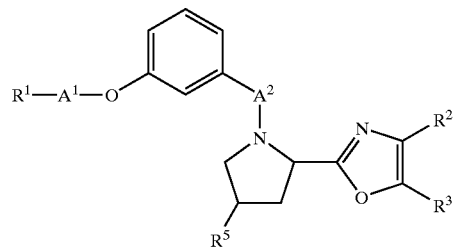

or its salt,
in the above formulas,
$R^1$, $R^2$, $R^3$, X, $A^1$ and $A^2$ are each as defined above,
Y is leaving group, or (2) subjecting a compound of the formula:

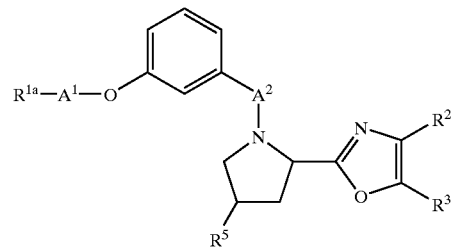

or its salt to elimination reaction to give a compound of the formula:

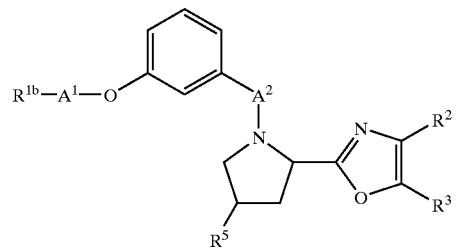

or its salt,
in the above formulas,
R, $R^3$, X, $A^1$ and $A^2$ are each as defined above,
$R^{1a}$ is lower alkoxycarbonyl, and
$R^{1b}$ is carboxy.

5. A pharmaceutical composition which comprises, as an active ingredient, a compound of claim 1 thereof in admixture with pharmaceutically acceptable carriers for treating arterial obstruction, restenosis or ischemic complications after coronary angioplasty, arteriosclerosis, cerebrovascular disease, ischemic heart disease, dermatosis or hepatic insufficiency.

6. A method, comprising:
treating a subject with a therapeutically effective amount of a compound of the formula:

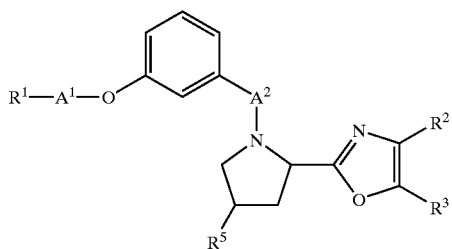

wherein
R¹ is carboxy or lower alkoxycarbonyl,
R² is phenyl or lower alkylphenyl,
R³ is phenyl or lower alkylphenyl, and
R⁵ is hydroxy or lower alkoxy, and
A¹ and A² are each independently methylene, thereby treating the conditions of thrombosis, arterial obstruction, cerebrovascular disease, gastric ulcer, hepatitis, hepatic insufficiency, hepatic cirrhosis, arteriosclerosis, ischemic heart disease, restenosis or ischemic complications after coronary angioplasty, hypertension, inflammation, autoimmune disease, heart failure, renal disease, diabetic complications, peripheral circulatory disturbance, dermatitis, chilblain, baldness, bedsores, inflammatory bowel disease, ischemic colitis or idiopathic inflammatory bowel disease.

* * * * *